United States Patent
Fink et al.

(10) Patent No.: US 9,227,000 B2
(45) Date of Patent: Jan. 5, 2016

(54) PORTABLE WOUND THERAPY SYSTEM

(71) Applicant: Smith & Nephew, Inc., Memphis, TN (US)

(72) Inventors: E. David Fink, Franklin, MA (US); David Heagle, Franklin, MA (US); Sharon A. Mulligan, Britsol, RI (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 14/134,802

(22) Filed: Dec. 19, 2013

(65) Prior Publication Data
US 2014/0107599 A1   Apr. 17, 2014

Related U.S. Application Data

(63) Continuation of application No. 11/904,411, filed on Sep. 27, 2007, now Pat. No. 8,641,691.

(60) Provisional application No. 60/847,886, filed on Sep. 28, 2006.

(51) Int. Cl.
*A61M 35/00* (2006.01)
*A61M 1/00* (2006.01)
(Continued)

(52) U.S. Cl.
CPC ........... *A61M 1/0023* (2013.01); *A61M 1/0001* (2013.01); *A61M 1/0015* (2014.02);
(Continued)

(58) Field of Classification Search
CPC ......... A61M 35/00; A61M 1/00; A61F 13/00; A61F 13/02; A61F 7/00
USPC ......... 604/289, 290, 305, 306, 307, 308, 313, 604/315, 316
See application file for complete search history.

(56) References Cited

U.S. PATENT DOCUMENTS

| 1,585,104 A | 5/1926 | Montgomery |
| 2,736,317 A | 2/1956 | Alexander |

(Continued)

FOREIGN PATENT DOCUMENTS

| AU | 674837 B2 | 1/1997 |
| CN | 101676563 | 3/2010 |

(Continued)

OTHER PUBLICATIONS

U.S. Appl. No. 14/142,635, filed Dec. 27, 2013, Weston.
(Continued)

*Primary Examiner* — Tatyana Zalukaeva
*Assistant Examiner* — Ilya Treyger
(74) *Attorney, Agent, or Firm* — Knobbe Martens Olson & Bear LLP

(57) ABSTRACT

A portable system for subatmospheric pressure therapy in connection with healing a surgical wound, includes a wound dressing dimensioned for positioning relative to a wound bed of a subject, a portable subatmospheric pressure mechanism dimensioned to be carried or worn by the subject and a container for collecting exudates from the wound bed removed under the subatmospheric pressure supplied by the subatmospheric pressure mechanism. The portable subatmospheric pressure mechanism includes a housing, a subatmospheric pressure source disposed within the housing and in fluid communication with the wound dressing to supply subatmospheric pressure to the wound dressing and a power source mounted to or within the housing for supplying power to actuate the subatmospheric pressure source.

21 Claims, 9 Drawing Sheets

(51) Int. Cl.
   *A61F 13/00* (2006.01)
   *A61F 13/02* (2006.01)
   *A61F 7/00* (2006.01)

(52) U.S. Cl.
   CPC ......... *A61M1/0088* (2013.01); *A61M 2205/15* (2013.01); *A61M 2209/082* (2013.01); *A61M 2209/088* (2013.01)

(56) References Cited

U.S. PATENT DOCUMENTS

| | | |
|---|---|---|
| 3,042,041 A | 7/1962 | Jascalevich |
| 3,568,675 A | 3/1971 | Harvey |
| 3,572,340 A | 3/1971 | Lloyd et al. |
| 3,787,882 A | 1/1974 | Fillmore et al. |
| 3,874,387 A | 4/1975 | Barbieri |
| 3,880,164 A | 4/1975 | Stepno |
| 3,972,328 A | 8/1976 | Chen |
| 4,015,912 A | 4/1977 | Kofink |
| 4,080,970 A | 3/1978 | Miller |
| 4,164,027 A | 8/1979 | Bonnie et al. |
| 4,231,357 A | 11/1980 | Hessner |
| 4,261,363 A | 4/1981 | Russo |
| 4,293,609 A | 10/1981 | Erickson |
| 4,321,020 A * | 3/1982 | Mittal .................. 417/320 |
| 4,360,015 A | 11/1982 | Mayer |
| 4,382,441 A | 5/1983 | Svedman |
| 4,392,853 A | 7/1983 | Muto |
| 4,460,642 A | 7/1984 | Errede et al. |
| 4,468,219 A | 8/1984 | George et al. |
| 4,540,412 A | 9/1985 | Van Overloop |
| 4,553,967 A | 11/1985 | Ferguson et al. |
| 4,561,435 A | 12/1985 | McKnight et al. |
| 4,569,674 A | 2/1986 | Phillips et al. |
| 4,578,060 A | 3/1986 | Huck et al. |
| 4,579,120 A | 4/1986 | MacGregor |
| 4,585,397 A * | 4/1986 | Crawford et al. .......... 417/63 |
| 4,599,052 A | 7/1986 | Langen et al. |
| 4,604,313 A | 8/1986 | McFarland et al. |
| 4,605,399 A | 8/1986 | Weston et al. |
| 4,614,183 A | 9/1986 | McCracken et al. |
| 4,643,641 A | 2/1987 | Clausen et al. |
| 4,846,164 A | 7/1989 | Martz |
| 4,906,240 A | 3/1990 | Reed et al. |
| 4,921,492 A | 5/1990 | Schultz et al. |
| 4,941,882 A | 7/1990 | Ward et al. |
| 4,969,880 A | 11/1990 | Zamierowski |
| 4,979,944 A | 12/1990 | Luzsicza |
| 4,980,226 A | 12/1990 | Hellgren et al. |
| 4,988,345 A | 1/1991 | Reising |
| 5,009,224 A | 4/1991 | Cole |
| 5,056,510 A | 10/1991 | Gilman |
| 5,060,642 A | 10/1991 | Gilman |
| 5,088,483 A | 2/1992 | Heinecke |
| 5,100,396 A | 3/1992 | Zamierowski |
| 5,106,362 A | 4/1992 | Gilman |
| 5,112,323 A | 5/1992 | Winkler et al. |
| 5,115,801 A | 5/1992 | Cartmell et al. |
| 5,134,007 A | 7/1992 | Reising et al. |
| 5,147,698 A | 9/1992 | Cole |
| 5,149,331 A | 9/1992 | Ferdman et al. |
| 5,152,757 A | 10/1992 | Eriksson |
| 5,160,315 A | 11/1992 | Heinecke et al. |
| 5,160,328 A | 11/1992 | Cartmell et al. |
| 5,160,334 A | 11/1992 | Billings et al. |
| 5,176,663 A | 1/1993 | Svedman et al. |
| 5,197,945 A | 3/1993 | Cole et al. |
| 5,222,714 A | 6/1993 | Morinigo et al. |
| 5,230,496 A | 7/1993 | Shillington et al. |
| 5,238,732 A | 8/1993 | Krishnan |
| 5,244,457 A | 9/1993 | Karami et al. |
| 5,246,353 A * | 9/1993 | Sohn .................. 417/413.1 |
| 5,261,893 A | 11/1993 | Zamierowski |
| 5,263,922 A | 11/1993 | Sova et al. |
| 5,300,054 A | 4/1994 | Feist et al. |
| 5,304,161 A | 4/1994 | Noel et al. |
| 5,308,313 A | 5/1994 | Karami et al. |
| 5,336,219 A | 8/1994 | Krantz |
| 5,354,261 A | 10/1994 | Clark et al. |
| 5,360,445 A * | 11/1994 | Goldowsky .................. 623/3.22 |
| 5,364,381 A | 11/1994 | Soga et al. |
| 5,366,451 A | 11/1994 | Levesque |
| 5,380,294 A | 1/1995 | Persson |
| 5,391,161 A | 2/1995 | Hellgren et al. |
| 5,437,651 A | 8/1995 | Todd et al. |
| 5,439,458 A | 8/1995 | Noel et al. |
| 5,447,492 A | 9/1995 | Cartmell et al. |
| 5,456,660 A | 10/1995 | Reich et al. |
| 5,470,585 A | 11/1995 | Gilchrist |
| 5,480,377 A | 1/1996 | Cartmell et al. |
| 5,486,167 A | 1/1996 | Dragoo et al. |
| 5,492,313 A | 2/1996 | Pan et al. |
| 5,497,788 A | 3/1996 | Inman et al. |
| 5,520,629 A | 5/1996 | Heinecke et al. |
| 5,525,407 A | 6/1996 | Yang |
| 5,527,293 A | 6/1996 | Zamierowski |
| 5,527,923 A | 6/1996 | Klingler et al. |
| 5,531,855 A | 7/1996 | Heinecke et al. |
| 5,538,500 A | 7/1996 | Peterson |
| 5,545,151 A | 8/1996 | O'Connor et al. |
| 5,549,584 A | 8/1996 | Gross |
| 5,562,107 A | 10/1996 | Lavender et al. |
| 5,579,765 A | 12/1996 | Cox et al. |
| 5,591,297 A | 1/1997 | Ahr |
| 5,593,750 A | 1/1997 | Rothrum et al. |
| 5,599,289 A | 2/1997 | Castellana |
| 5,603,946 A | 2/1997 | Constantine |
| 5,613,942 A | 3/1997 | Lucast et al. |
| 5,618,278 A | 4/1997 | Rothrum |
| 5,624,423 A | 4/1997 | Anjur et al. |
| 5,630,855 A | 5/1997 | Lundbaeck |
| 5,636,643 A | 6/1997 | Argenta et al. |
| 5,637,080 A | 6/1997 | Geng |
| 5,637,093 A | 6/1997 | Hyman et al. |
| 5,645,081 A | 7/1997 | Argenta et al. |
| 5,662,599 A | 9/1997 | Reich et al. |
| 5,678,564 A | 10/1997 | Lawrence et al. |
| 5,688,516 A | 11/1997 | Raad et al. |
| 5,695,846 A | 12/1997 | Lange et al. |
| 5,702,356 A | 12/1997 | Hathman |
| 5,704,905 A | 1/1998 | Jensen et al. |
| 5,707,173 A | 1/1998 | Cottone et al. |
| 5,713,384 A | 2/1998 | Roach et al. |
| 5,730,587 A | 3/1998 | Snyder et al. |
| 5,738,642 A | 4/1998 | Heinecke et al. |
| 5,759,570 A | 6/1998 | Arnold |
| 5,762,638 A | 6/1998 | Shikani et al. |
| 5,769,608 A | 6/1998 | Seale |
| 5,795,584 A | 8/1998 | Totakura et al. |
| 5,797,844 A | 8/1998 | Yoshioka et al. |
| 5,797,894 A | 8/1998 | Cadieux et al. |
| 5,827,213 A | 10/1998 | Jensen |
| 5,840,052 A | 11/1998 | Johns |
| 5,843,025 A | 12/1998 | Shaari |
| 5,882,743 A | 3/1999 | McConnell |
| 5,894,608 A | 4/1999 | Birbara |
| 5,897,296 A | 4/1999 | Yamamoto et al. |
| 5,897,541 A | 4/1999 | Uitenbrock et al. |
| 5,914,282 A | 6/1999 | Dunshee et al. |
| 6,040,493 A | 3/2000 | Cooke et al. |
| 6,056,519 A | 5/2000 | Morita et al. |
| 6,068,588 A | 5/2000 | Goldowsky |
| 6,071,267 A | 6/2000 | Zamierowski |
| 6,075,177 A | 6/2000 | Bahia et al. |
| 6,102,205 A | 8/2000 | Greff et al. |
| 6,117,111 A | 9/2000 | Fleischmann |
| 6,121,508 A | 9/2000 | Bischof et al. |
| 6,124,520 A | 9/2000 | Roberts |
| 6,124,521 A | 9/2000 | Roberts |
| 6,142,982 A | 11/2000 | Hunt et al. |
| 6,169,224 B1 | 1/2001 | Heinecke et al. |
| 6,174,136 B1 | 1/2001 | Kilayko et al. |
| 6,231,310 B1 | 5/2001 | Tojo et al. |
| 6,249,198 B1 | 6/2001 | Clark et al. |

(56) References Cited

U.S. PATENT DOCUMENTS

| | | | |
|---|---|---|---|
| 6,264,976 B1 | 7/2001 | Heinecke et al. |
| 6,291,050 B1 | 9/2001 | Cree et al. |
| 6,297,423 B1 | 10/2001 | Schoenfeldt et al. |
| 6,323,568 B1 | 11/2001 | Zabar |
| 6,345,623 B1 | 2/2002 | Heaton et al. |
| 6,362,390 B1 | 3/2002 | Carlucci et al. |
| 6,406,447 B1 | 6/2002 | Thrash et al. |
| 6,413,057 B1 | 7/2002 | Hong et al. |
| 6,420,622 B1 | 7/2002 | Johnston et al. |
| 6,436,432 B2 | 8/2002 | Heinecke et al. |
| 6,458,109 B1 | 10/2002 | Henley et al. |
| 6,461,467 B2 | 10/2002 | Blatchford et al. |
| 6,479,073 B1 | 11/2002 | Lucast et al. |
| 6,506,175 B1 | 1/2003 | Goldstein |
| 6,514,047 B2 | 2/2003 | Burr et al. |
| 6,528,696 B1 | 3/2003 | Ireland |
| 6,540,490 B1 | 4/2003 | Lilie |
| 6,553,998 B2 | 4/2003 | Heaton et al. |
| 6,566,575 B1 | 5/2003 | Stickels et al. |
| 6,589,028 B1 | 7/2003 | Eckerbom et al. |
| 6,604,908 B1 | 8/2003 | Bryant et al. |
| 6,607,799 B1 | 8/2003 | Heinecke et al. |
| 6,613,953 B1 | 9/2003 | Altura |
| 6,618,221 B2 | 9/2003 | Gillis et al. |
| 6,623,255 B2 | 9/2003 | Joong et al. |
| 6,626,891 B2 | 9/2003 | Ohmstede |
| 6,638,035 B1 | 10/2003 | Puff |
| 6,648,862 B2 | 11/2003 | Watson |
| 6,652,252 B2 | 11/2003 | Zabar |
| 6,685,681 B2 | 2/2004 | Lockwood et al. |
| 6,685,682 B1 | 2/2004 | Heinecke et al. |
| 6,719,742 B1 | 4/2004 | McCormack et al. |
| 6,752,794 B2 | 6/2004 | Lockwood et al. |
| 6,755,807 B2 | 6/2004 | Risk, Jr. et al. |
| 6,764,459 B1 | 7/2004 | Donaldson |
| 6,800,074 B2 | 10/2004 | Henley et al. |
| 6,814,079 B2 | 11/2004 | Heaton et al. |
| 6,815,846 B2 | 11/2004 | Godkin |
| 6,824,533 B2 | 11/2004 | Risk, Jr. et al. |
| 6,838,589 B2 | 1/2005 | Liedtke et al. |
| 6,855,135 B2 | 2/2005 | Lockwood et al. |
| 6,867,342 B2 | 3/2005 | Johnston et al. |
| 6,878,857 B1 | 4/2005 | Chihani et al. |
| 6,885,116 B2 * | 4/2005 | Knirck et al. ............... 310/12.04 |
| 6,903,243 B1 | 6/2005 | Burton |
| 6,936,037 B2 | 8/2005 | Bubb et al. |
| 6,951,553 B2 | 10/2005 | Bubb et al. |
| 6,979,324 B2 | 12/2005 | Bybordi et al. |
| 6,994,702 B1 | 2/2006 | Johnson |
| 6,994,904 B2 | 2/2006 | Joseph et al. |
| 7,004,915 B2 | 2/2006 | Boynton et al. |
| 7,005,143 B2 | 2/2006 | Abuelyaman et al. |
| 7,049,478 B1 | 5/2006 | Smith et al. |
| 7,070,580 B2 | 7/2006 | Nielsen |
| 7,070,584 B2 | 7/2006 | Johnson et al. |
| 7,108,683 B2 | 9/2006 | Zamierowski |
| 7,117,869 B2 | 10/2006 | Heaton |
| 7,128,735 B2 | 10/2006 | Weston |
| 7,151,348 B1 | 12/2006 | Ueda et al. |
| 7,183,454 B1 | 2/2007 | Rosenberg |
| 7,195,624 B2 | 3/2007 | Lockwood et al. |
| 7,198,046 B1 | 4/2007 | Argenta et al. |
| 7,216,651 B2 | 5/2007 | Argenta et al. |
| 7,273,054 B2 | 9/2007 | Heaton et al. |
| 7,276,247 B2 | 10/2007 | Fansler et al. |
| 7,279,612 B1 | 10/2007 | Heaton et al. |
| 7,285,576 B2 | 10/2007 | Hyde et al. |
| 7,294,752 B1 | 11/2007 | Propp |
| 7,316,672 B1 | 1/2008 | Hunt et al. |
| 7,338,482 B2 | 3/2008 | Lockwood et al. |
| 7,361,184 B2 | 4/2008 | Joshi |
| 7,374,409 B2 | 5/2008 | Kawamura |
| 7,381,859 B2 | 6/2008 | Hunt et al. |
| 7,401,703 B2 | 7/2008 | McMichael et al. |
| 7,438,705 B2 | 10/2008 | Karpowicz et al. |
| 7,442,849 B2 | 10/2008 | Heinecke |
| 7,485,112 B2 | 2/2009 | Karpowicz et al. |
| 7,503,910 B2 | 3/2009 | Adahan |
| 7,524,315 B2 | 4/2009 | Blott et al. |
| 7,534,927 B2 | 5/2009 | Lockwood et al. |
| 7,550,034 B2 | 6/2009 | Janse Van Rensburg et al. |
| 7,569,742 B2 | 8/2009 | Haggstrom et al. |
| 7,585,554 B2 | 9/2009 | Johnson et al. |
| 7,586,019 B2 | 9/2009 | Oelund et al. |
| 7,615,036 B2 | 11/2009 | Joshi et al. |
| 7,625,362 B2 | 12/2009 | Boehringer et al. |
| 7,645,269 B2 | 1/2010 | Zamierowski |
| 7,670,323 B2 | 3/2010 | Hunt et al. |
| 7,678,102 B1 | 3/2010 | Heaton |
| 7,686,785 B2 | 3/2010 | Boehringer et al. |
| 7,699,823 B2 | 4/2010 | Haggstrom et al. |
| 7,708,724 B2 | 5/2010 | Weston |
| 7,723,560 B2 | 5/2010 | Lockwood et al. |
| 7,745,681 B1 | 6/2010 | Ferguson |
| 7,754,937 B2 | 7/2010 | Boehringer et al. |
| 7,758,554 B2 | 7/2010 | Lina et al. |
| 7,759,537 B2 | 7/2010 | Bishop et al. |
| 7,759,539 B2 | 7/2010 | Shaw et al. |
| 7,779,625 B2 | 8/2010 | Joshi et al. |
| 7,781,639 B2 | 8/2010 | Johnston et al. |
| 7,785,247 B2 | 8/2010 | Tatum et al. |
| 7,794,438 B2 | 9/2010 | Henley et al. |
| 7,811,269 B2 | 10/2010 | Boynton et al. |
| 7,815,616 B2 | 10/2010 | Boehringer et al. |
| 7,838,717 B2 | 11/2010 | Haggstrom et al. |
| 7,846,141 B2 | 12/2010 | Weston |
| 7,857,806 B2 | 12/2010 | Karpowicz et al. |
| 7,862,718 B2 | 1/2011 | Doyen et al. |
| 7,896,864 B2 | 3/2011 | Lockwood et al. |
| 7,909,805 B2 | 3/2011 | Weston |
| 7,910,791 B2 | 3/2011 | Coffey |
| 7,922,703 B2 | 4/2011 | Riesinger |
| 7,942,866 B2 | 5/2011 | Radl et al. |
| 7,951,124 B2 | 5/2011 | Boehringer et al. |
| 7,959,624 B2 | 6/2011 | Riesinger |
| 7,964,766 B2 | 6/2011 | Blott et al. |
| 7,976,533 B2 | 7/2011 | Larsson |
| 7,981,098 B2 | 7/2011 | Boehringer et al. |
| 8,002,313 B2 | 8/2011 | Singh et al. |
| 8,048,046 B2 | 11/2011 | Hudspeth et al. |
| 8,062,272 B2 | 11/2011 | Weston |
| 8,105,295 B2 | 1/2012 | Blott et al. |
| 8,142,419 B2 | 3/2012 | Heaton et al. |
| 8,158,844 B2 | 4/2012 | McNeil |
| 8,162,907 B2 | 4/2012 | Heagle |
| 8,167,869 B2 | 5/2012 | Wudyka |
| 8,186,978 B2 | 5/2012 | Tinholt et al. |
| 8,188,331 B2 | 5/2012 | Barta et al. |
| 8,207,392 B2 | 6/2012 | Haggstrom et al. |
| 8,215,929 B2 | 7/2012 | Shen et al. |
| 8,241,015 B2 | 8/2012 | Lillie |
| 8,257,327 B2 | 9/2012 | Blott et al. |
| 8,350,116 B2 | 1/2013 | Lockwood et al. |
| 8,363,881 B2 | 1/2013 | Godkin |
| 8,398,614 B2 | 3/2013 | Blott et al. |
| 8,409,157 B2 | 4/2013 | Haggstrom et al. |
| 8,409,160 B2 | 4/2013 | Locke et al. |
| 8,414,519 B2 | 4/2013 | Hudspeth et al. |
| 8,429,778 B2 | 4/2013 | Receveur et al. |
| 8,444,612 B2 | 5/2013 | Patel et al. |
| 8,545,464 B2 | 10/2013 | Weston |
| 8,569,566 B2 | 10/2013 | Blott et al. |
| 8,604,265 B2 | 12/2013 | Locke et al. |
| 8,795,257 B2 | 8/2014 | Coulthard et al. |
| 8,814,842 B2 | 8/2014 | Coulthard et al. |
| 2001/0001278 A1 | 5/2001 | Drevet |
| 2001/0033795 A1 | 10/2001 | Humpheries |
| 2001/0034223 A1 | 10/2001 | Rieser et al. |
| 2001/0043870 A1 | 11/2001 | Song |
| 2002/0002209 A1 | 1/2002 | Mork |
| 2002/0115952 A1 | 8/2002 | Johnson et al. |
| 2002/0122732 A1 | 9/2002 | Oh et al. |
| 2002/0164255 A1 | 11/2002 | Burr et al. |
| 2002/0182246 A1 | 12/2002 | Oyaski |

(56) References Cited

U.S. PATENT DOCUMENTS

| | | |
|---|---|---|
| 2003/0035743 A1 | 2/2003 | Lee et al. |
| 2003/0065292 A1 | 4/2003 | Darouiche |
| 2003/0095879 A1 | 5/2003 | Oh et al. |
| 2003/0097100 A1 | 5/2003 | Watson |
| 2003/0099558 A1 | 5/2003 | Chang |
| 2003/0108430 A1 | 6/2003 | Yoshida et al. |
| 2003/0133812 A1 | 7/2003 | Puff et al. |
| 2003/0161735 A1 | 8/2003 | Kim et al. |
| 2003/0162071 A1 | 8/2003 | Yasuda |
| 2003/0175125 A1 | 9/2003 | Kwon et al. |
| 2003/0175135 A1 | 9/2003 | Heo et al. |
| 2004/0005222 A1 | 1/2004 | Yoshida et al. |
| 2004/0021123 A1 | 2/2004 | Howell et al. |
| 2004/0039415 A1 | 2/2004 | Zamierowski |
| 2004/0054338 A1 | 3/2004 | Bybordi et al. |
| 2004/0064132 A1 | 4/2004 | Boehringer et al. |
| 2004/0066097 A1 | 4/2004 | Kobayashi et al. |
| 2004/0071568 A1 | 4/2004 | Hyeon |
| 2004/0073151 A1 | 4/2004 | Weston |
| 2004/0115076 A1 | 6/2004 | Lilie et al. |
| 2004/0116551 A1 | 6/2004 | Terry |
| 2004/0126250 A1 | 7/2004 | Tsuchiya et al. |
| 2004/0155741 A1 | 8/2004 | Godin |
| 2004/0156730 A1 | 8/2004 | Lilie et al. |
| 2004/0189103 A1 | 9/2004 | Duncan et al. |
| 2005/0004534 A1 | 1/2005 | Lockwood et al. |
| 2005/0010153 A1 | 1/2005 | Lockwood et al. |
| 2005/0020955 A1 | 1/2005 | Sanders et al. |
| 2005/0031470 A1 | 2/2005 | Lee |
| 2005/0065484 A1 | 3/2005 | Watson Jr. |
| 2005/0070858 A1 | 3/2005 | Lockwood et al. |
| 2005/0085795 A1 | 4/2005 | Lockwood et al. |
| 2005/0098031 A1 | 5/2005 | Yoon et al. |
| 2005/0100450 A1 | 5/2005 | Bryant et al. |
| 2005/0111987 A1 | 5/2005 | Yoo et al. |
| 2005/0123422 A1 | 6/2005 | Lilie |
| 2005/0129540 A1 | 6/2005 | Puff |
| 2005/0135946 A1 | 6/2005 | Kang et al. |
| 2005/0137539 A1 | 6/2005 | Biggie et al. |
| 2005/0142007 A1 | 6/2005 | Lee et al. |
| 2005/0142008 A1 | 6/2005 | Jung et al. |
| 2005/0163635 A1 | 7/2005 | Berwanger et al. |
| 2005/0203452 A1 | 9/2005 | Weston et al. |
| 2005/0222527 A1 | 10/2005 | Miller et al. |
| 2005/0271526 A1 | 12/2005 | Chang et al. |
| 2005/0273066 A1 | 12/2005 | Wittmann |
| 2005/0276706 A1 | 12/2005 | Radue |
| 2006/0009744 A1 | 1/2006 | Erdman et al. |
| 2006/0017332 A1 | 1/2006 | Kang et al. |
| 2006/0018771 A1 | 1/2006 | Song et al. |
| 2006/0024181 A1 | 2/2006 | Kim |
| 2006/0025727 A1 | 2/2006 | Boehringer et al. |
| 2006/0036221 A1 | 2/2006 | Watson Jr. |
| 2006/0041247 A1 | 2/2006 | Petrosenko et al. |
| 2006/0056979 A1 | 3/2006 | Yoo et al. |
| 2006/0056980 A1 | 3/2006 | Yoo et al. |
| 2006/0057000 A1 | 3/2006 | Hyeon |
| 2006/0061024 A1 | 3/2006 | Jung et al. |
| 2006/0079852 A1 | 4/2006 | Bubb et al. |
| 2006/0100586 A1 | 5/2006 | Karpowicz et al. |
| 2006/0110259 A1 | 5/2006 | Puff et al. |
| 2006/0210411 A1 | 9/2006 | Hyeon |
| 2006/0216165 A1 | 9/2006 | Lee |
| 2006/0222532 A1 | 10/2006 | Lee et al. |
| 2006/0228224 A1 | 10/2006 | Hong et al. |
| 2006/0251523 A1 | 11/2006 | Lee et al. |
| 2006/0271020 A1 | 11/2006 | Huang et al. |
| 2007/0038172 A1 | 2/2007 | Zamierowski |
| 2007/0040454 A1 | 2/2007 | Freudenberger et al. |
| 2007/0041856 A1 | 2/2007 | Hansen et al. |
| 2007/0052144 A1 | 3/2007 | Knirck et al. |
| 2007/0055209 A1 | 3/2007 | Patel et al. |
| 2007/0141128 A1 | 6/2007 | Blott et al. |
| 2007/0156104 A1 | 7/2007 | Lockwood et al. |
| 2007/0167927 A1 | 7/2007 | Hunt et al. |
| 2007/0196214 A1 | 8/2007 | Bocchiola |
| 2007/0219497 A1 | 9/2007 | Johnson et al. |
| 2007/0225663 A1 | 9/2007 | Watt et al. |
| 2007/0233022 A1 | 10/2007 | Henley et al. |
| 2007/0256428 A1 | 11/2007 | Unger et al. |
| 2007/0292286 A1 | 12/2007 | Hell et al. |
| 2007/0295201 A1 | 12/2007 | Dadd |
| 2008/0008607 A1 | 1/2008 | Schade et al. |
| 2008/0082059 A1 | 4/2008 | Fink et al. |
| 2008/0089796 A1 | 4/2008 | Schade et al. |
| 2008/0119802 A1 | 5/2008 | Riesinger |
| 2008/0167593 A1 | 7/2008 | Fleischmann |
| 2008/0191399 A1 | 8/2008 | Chang |
| 2008/0211435 A1 | 9/2008 | Imagawa |
| 2008/0240942 A1 | 10/2008 | Heinrich et al. |
| 2008/0267797 A1 | 10/2008 | Hell et al. |
| 2008/0281281 A1 | 11/2008 | Meyer et al. |
| 2008/0306456 A1 | 12/2008 | Riesinger |
| 2009/0005744 A1 | 1/2009 | Karpowicz et al. |
| 2009/0012501 A1 | 1/2009 | Boehringer et al. |
| 2009/0054855 A1 | 2/2009 | Blott et al. |
| 2009/0060750 A1 | 3/2009 | Chen et al. |
| 2009/0081049 A1 | 3/2009 | Tian et al. |
| 2009/0087323 A1 | 4/2009 | Blakey et al. |
| 2009/0125004 A1 | 5/2009 | Shen et al. |
| 2009/0129955 A1 | 5/2009 | Schubert |
| 2009/0131892 A1 | 5/2009 | Karpowicz et al. |
| 2009/0137973 A1 | 5/2009 | Karpowicz et al. |
| 2009/0148320 A1 | 6/2009 | Lucas |
| 2009/0157016 A1 | 6/2009 | Adahan |
| 2009/0169402 A1 | 7/2009 | Stenberg |
| 2009/0192467 A1 | 7/2009 | Hansen et al. |
| 2009/0192499 A1 | 7/2009 | Weston et al. |
| 2009/0206778 A1 | 8/2009 | Roh et al. |
| 2009/0264837 A1 | 10/2009 | Adahan |
| 2009/0299306 A1 | 12/2009 | Buan |
| 2010/0016767 A1 | 1/2010 | Jones et al. |
| 2010/0098566 A1 | 4/2010 | Kang |
| 2010/0160878 A1 | 6/2010 | Hunt et al. |
| 2010/0160881 A1 | 6/2010 | Lin et al. |
| 2010/0210986 A1 | 8/2010 | Sanders |
| 2010/0320659 A1 | 12/2010 | Chen et al. |
| 2011/0028918 A1 | 2/2011 | Hartwell |
| 2011/0043055 A1 | 2/2011 | Chiang |
| 2011/0054421 A1 | 3/2011 | Hartwell |
| 2011/0081267 A1 | 4/2011 | McCrone et al. |
| 2011/0169348 A1 | 7/2011 | Park |
| 2011/0176946 A1 | 7/2011 | Drevet |
| 2011/0205646 A1 | 8/2011 | Sato et al. |
| 2011/0205647 A1 | 8/2011 | Osaka et al. |
| 2011/0237863 A1 | 9/2011 | Ricci et al. |
| 2011/0282309 A1 | 11/2011 | Adie et al. |
| 2012/0000208 A1 | 1/2012 | Hon et al. |
| 2012/0034109 A1 | 2/2012 | Tout et al. |
| 2012/0053543 A1 | 3/2012 | Miau et al. |
| 2012/0109083 A1 | 5/2012 | Coulthard et al. |
| 2012/0160091 A1 | 6/2012 | Dadd et al. |
| 2012/0177513 A1 | 7/2012 | Lilie et al. |
| 2012/0251359 A1 | 10/2012 | Neelakantan et al. |
| 2013/0110058 A1 | 5/2013 | Adie et al. |
| 2013/0116635 A1 | 5/2013 | Fleischmann |
| 2013/0138054 A1 | 5/2013 | Fleischmann |
| 2013/0138060 A1 | 5/2013 | Haggstrom et al. |
| 2013/0331822 A1 | 12/2013 | Patel |
| 2013/0331823 A1 | 12/2013 | Askem |
| 2013/0338613 A1 | 12/2013 | Haggstrom et al. |
| 2014/0018753 A1 | 1/2014 | Joshi et al. |

FOREIGN PATENT DOCUMENTS

| | | |
|---|---|---|
| DE | 39 16 648 | 9/1990 |
| DE | 3907007 | 9/1990 |
| DE | 90 17 289 | 6/1992 |
| DE | 198 44 355 | 4/2000 |
| DE | 10 2005 007016 | 8/2006 |
| DE | 20 2010 009 148 | 10/2010 |
| EP | 0 411 564 | 2/1991 |
| EP | 0465601 B1 | 1/1992 |
| EP | 0 541 251 | 5/1993 |

(56) References Cited

FOREIGN PATENT DOCUMENTS

| | | |
|---|---|---|
| EP | 0325771 B1 | 9/1993 |
| EP | 0 578 999 | 1/1994 |
| EP | 0392640 B1 | 6/1995 |
| EP | 0441418 B1 | 7/1995 |
| EP | 0688189 B2 | 12/1995 |
| EP | 0751757 B1 | 1/1997 |
| EP | 0 793 019 | 9/1997 |
| EP | 0692987 B1 | 10/1997 |
| EP | 0651983 B1 | 9/1998 |
| EP | 0777504 B1 | 10/1998 |
| EP | 0782421 B1 | 7/1999 |
| EP | 0 941 726 | 9/1999 |
| EP | 0690706 B1 | 11/2000 |
| EP | 1 114 933 | 7/2001 |
| EP | 1129734 A2 | 9/2001 |
| EP | 0921775 B1 | 12/2001 |
| EP | 1 169 071 A1 | 1/2002 |
| EP | 0853950 B1 | 10/2002 |
| EP | 0 909 895 | 12/2002 |
| EP | 1 283 702 A1 | 2/2003 |
| EP | 0708620 B1 | 5/2003 |
| EP | 1014905 B1 | 5/2003 |
| EP | 0993317 B1 | 9/2003 |
| EP | 0880953 B1 | 10/2003 |
| EP | 1 406 020 | 4/2004 |
| EP | 1 430 588 | 6/2004 |
| EP | 1219311 B1 | 7/2004 |
| EP | 1018967 | 8/2004 |
| EP | 1 452 156 | 9/2004 |
| EP | 1100574 B1 | 2/2005 |
| EP | 1 517 660 A2 | 3/2005 |
| EP | 1 556 942 | 5/2005 |
| EP | 1 554 737 | 7/2005 |
| EP | 1 556 120 A2 | 7/2005 |
| EP | 1 565 219 A2 | 8/2005 |
| EP | 1440667 | 3/2006 |
| EP | 1284777 B1 | 4/2006 |
| EP | 0982015 B1 | 8/2006 |
| EP | 0620720 B2 | 11/2006 |
| EP | 1 757 809 | 2/2007 |
| EP | 1448261 | 2/2007 |
| EP | 1171065 | 3/2007 |
| EP | 1809350 | 7/2007 |
| EP | 1 850 005 | 10/2007 |
| EP | 1227853 B1 | 1/2008 |
| EP | 1476217 B1 | 3/2008 |
| EP | 1904137 | 4/2008 |
| EP | 1920791 A2 | 5/2008 |
| EP | 1931413 | 6/2008 |
| EP | 1233808 B1 | 7/2008 |
| EP | 1977776 | 10/2008 |
| EP | 1986584 | 11/2008 |
| EP | 1986718 | 11/2008 |
| EP | 1993652 | 11/2008 |
| EP | 1993653 | 11/2008 |
| EP | 1827561 B1 | 1/2009 |
| EP | 2037852 | 3/2009 |
| EP | 2052750 A1 | 4/2009 |
| EP | 2068798 | 6/2009 |
| EP | 1496822 | 8/2009 |
| EP | 2 129 915 | 12/2009 |
| EP | 1513478 B1 | 12/2009 |
| EP | 1652549 B1 | 1/2010 |
| EP | 1905465 B1 | 1/2010 |
| EP | 2 161 011 | 3/2010 |
| EP | 2 161 448 | 3/2010 |
| EP | 2127690 A2 | 3/2010 |
| EP | 2172164 | 4/2010 |
| EP | 2254537 | 12/2010 |
| EP | 1703922 B1 | 5/2011 |
| EP | 1578477 B1 | 9/2011 |
| EP | 1487389 | 10/2011 |
| EP | 1169071 | 2/2012 |
| EP | 1660000 | 10/2012 |
| EP | 2 531 160 | 12/2012 |
| EP | 2 531 761 | 12/2012 |
| EP | 2545946 | 3/2013 |
| EP | 2 577 062 | 4/2013 |
| EP | 1339366 | 6/2014 |
| EP | 2051675 | 6/2014 |
| EP | 1478313 | 8/2014 |
| FR | 1163907 | 10/1958 |
| FR | 2 939 320 | 6/2010 |
| GB | 1 039 145 | 8/1966 |
| GB | 1 220 857 | 1/1971 |
| GB | 2 099 306 | 12/1982 |
| GB | 2 235 877 | 3/1991 |
| GB | 2 273 133 | 6/1994 |
| GB | 2 306 580 | 5/1997 |
| GB | 2307180 B2 | 6/2000 |
| GB | 2336546 B2 | 6/2000 |
| GB | 2356148 B2 | 6/2004 |
| GB | 2431351 A1 | 4/2007 |
| GB | 2 435 422 | 8/2007 |
| JP | 52-040804 | 3/1977 |
| JP | 2000-220570 | 8/2000 |
| JP | 2006-233925 | 9/2006 |
| WO | WO 87/07683 | 12/1987 |
| WO | WO 94/03214 | 2/1994 |
| WO | WO 94/23677 | 10/1994 |
| WO | WO 94/23678 | 10/1994 |
| WO | WO 95/04511 | 2/1995 |
| WO | WO 95/14451 | 6/1995 |
| WO | WO 96/21410 | 7/1996 |
| WO | WO 97/11658 | 4/1997 |
| WO | WO 97/18007 | 5/1997 |
| WO | WO 99/01173 | 1/1999 |
| WO | WO 99/39671 | 8/1999 |
| WO | WO 00/07653 | 2/2000 |
| WO | WO 00/22298 | 4/2000 |
| WO | WO 00/42957 | 7/2000 |
| WO | WO 00/61206 | 10/2000 |
| WO | WO 01/16488 | 3/2001 |
| WO | WO 01/79693 | 10/2001 |
| WO | WO 01/85228 | 11/2001 |
| WO | WO 01/85248 | 11/2001 |
| WO | WO 02/17840 | 3/2002 |
| WO | WO 02/26180 | 4/2002 |
| WO | WO 02/38096 | 5/2002 |
| WO | WO 02/43634 | 6/2002 |
| WO | WO 02/070040 | 9/2002 |
| WO | WO 02/076379 | 10/2002 |
| WO | WO 02/087058 | 10/2002 |
| WO | WO 02/090772 | 11/2002 |
| WO | WO 03/001898 | 3/2003 |
| WO | WO 03/057071 | 7/2003 |
| WO | WO 03/057307 | 7/2003 |
| WO | WO 03/085810 | 10/2003 |
| WO | WO 03/086232 | 10/2003 |
| WO | WO 03/101508 | 12/2003 |
| WO | WO 2004/000409 | 12/2003 |
| WO | WO 2004/018020 | 3/2004 |
| WO | WO 2004/037334 | 5/2004 |
| WO | WO 2004/041064 | 5/2004 |
| WO | WO 2004/060148 | 7/2004 |
| WO | WO 2004/060225 | 7/2004 |
| WO | WO 94/21207 | 9/2004 |
| WO | WO 2004/073566 | 9/2004 |
| WO | WO 2004/081421 | 9/2004 |
| WO | WO 2005/001286 | 1/2005 |
| WO | WO 2005/001287 | 1/2005 |
| WO | WO 2005/009488 | 2/2005 |
| WO | WO 2005/016179 | 2/2005 |
| WO | WO 2005/025447 | 3/2005 |
| WO | WO 2005/046760 | 5/2005 |
| WO | WO 2005/046761 | 5/2005 |
| WO | WO 2005/046762 | 5/2005 |
| WO | WO 2005/051461 | 6/2005 |
| WO | WO 2005/061025 | 7/2005 |
| WO | WO 2005/072789 | 8/2005 |
| WO | WO 2005/079718 | 9/2005 |
| WO | WO 2005/102415 | 11/2005 |
| WO | WO 2005/105174 | 11/2005 |
| WO | WO 2005/105175 | 11/2005 |

(56) References Cited

FOREIGN PATENT DOCUMENTS

| | | |
|---|---|---|
| WO | WO 2005/105176 | 11/2005 |
| WO | WO 2005/105179 | 11/2005 |
| WO | WO 2005/105180 | 11/2005 |
| WO | WO 2005/115497 | 12/2005 |
| WO | WO 2005/115523 | 12/2005 |
| WO | WO 2005/123170 | 12/2005 |
| WO | WO 2006/046060 | 5/2006 |
| WO | WO 2006/052338 | 5/2006 |
| WO | WO 2006/052745 | 5/2006 |
| WO | WO 2006/052839 | 5/2006 |
| WO | WO 2006/059098 | 6/2006 |
| WO | WO 2006/062276 | 6/2006 |
| WO | WO 2006/069884 | 7/2006 |
| WO | WO 2006/069885 | 7/2006 |
| WO | WO 2006/114637 | 11/2006 |
| WO | WO 2006/114638 | 11/2006 |
| WO | WO 2006/114648 | 11/2006 |
| WO | WO 2006/122268 | 11/2006 |
| WO | WO 2007/006306 | 1/2007 |
| WO | WO 2007/013049 | 2/2007 |
| WO | WO 2007/015964 | 2/2007 |
| WO | WO 2007/016590 | 2/2007 |
| WO | WO 2007/019038 | 2/2007 |
| WO | WO 2007/030598 | 3/2007 |
| WO | WO 2007/030599 | 3/2007 |
| WO | WO 2007/030601 | 3/2007 |
| WO | WO 2007/031757 | 3/2007 |
| WO | WO 2007/031762 | 3/2007 |
| WO | WO 2007/031765 | 3/2007 |
| WO | WO 2007/041642 | 4/2007 |
| WO | WO 2007/049876 | 5/2007 |
| WO | WO 2007/062024 | 5/2007 |
| WO | WO 2007/067359 | 6/2007 |
| WO | WO 2007/067685 | 6/2007 |
| WO | WO 2007/085396 | 8/2007 |
| WO | WO 2007/087808 | 8/2007 |
| WO | WO 2007/087809 | 8/2007 |
| WO | WO 2007/087810 | 8/2007 |
| WO | WO 2007/087811 | 8/2007 |
| WO | WO 2007/092397 | 8/2007 |
| WO | WO 2007/095180 | 8/2007 |
| WO | WO 2007/106590 | 9/2007 |
| WO | WO 2007/106591 | 9/2007 |
| WO | WO 2007/133618 | 11/2007 |
| WO | WO 2007/143060 | 12/2007 |
| WO | WO 2008/008032 | 1/2008 |
| WO | WO 2008/010094 | 1/2008 |
| WO | WO 2008/011774 | 1/2008 |
| WO | WO 2008/012278 | 1/2008 |
| WO | WO 2008/013896 | 1/2008 |
| WO | WO 2008/014358 | 1/2008 |
| WO | WO 2008/016304 | 2/2008 |
| WO | WO 2008/036162 | 3/2008 |
| WO | WO 2008/040020 | 4/2008 |
| WO | WO 2008/049277 | 5/2008 |
| WO | WO 2008/100440 | 8/2008 |
| WO | WO 2008/110022 | 8/2008 |
| WO | WO 2008/131895 | 11/2008 |
| WO | WO 2008/135997 | 11/2008 |
| WO | WO 2009/019415 | 2/2009 |
| WO | WO 2009/146441 | 3/2009 |
| WO | WO 2009/047524 | 4/2009 |
| WO | WO 2009/066104 | 5/2009 |
| WO | WO 2009/071929 | 6/2009 |
| WO | WO 2009/071935 | 6/2009 |
| WO | WO 2009/089390 | 7/2009 |
| WO | WO 2009/095170 | 8/2009 |
| WO | WO 2009/124100 | 10/2009 |
| WO | WO 2009/126103 | 10/2009 |
| WO | WO 2010/039481 | 4/2010 |
| WO | WO 2010/079359 | 7/2010 |
| WO | WO 2010/082872 | 7/2010 |
| WO | WO 2010/089448 | 8/2010 |
| WO | WO 2010/093753 | 8/2010 |
| WO | WO 2010/126444 | 11/2010 |
| WO | WO 2010/139926 | 12/2010 |
| WO | WO 2011/023650 | 3/2011 |
| WO | WO 2011/082461 | 7/2011 |
| WO | WO 2011/097361 | 8/2011 |
| WO | WO 2011/097362 | 8/2011 |
| WO | WO 2011/087871 | 10/2011 |
| WO | WO 2011/128651 | 10/2011 |
| WO | WO 2011/146535 | 11/2011 |
| WO | WO 2011/148188 | 12/2011 |
| WO | WO 2011/150529 | 12/2011 |
| WO | WO 2012/009370 | 1/2012 |
| WO | WO 2012/034238 | 3/2012 |
| WO | WO 2012/048179 | 4/2012 |
| WO | WO 2012/074512 | 6/2012 |
| WO | WO 2012/088572 | 7/2012 |
| WO | WO 2012/095245 | 7/2012 |
| WO | WO 2012/146656 | 11/2012 |
| WO | WO 2012/150235 | 11/2012 |
| WO | WO 2013/007973 | 1/2013 |
| WO | WO 2013/149078 | 10/2013 |
| WO | WO 2013/136181 | 11/2013 |
| WO | WO 2013/171585 | 11/2013 |

OTHER PUBLICATIONS

Morcos, Anthony C.; Voice Coil Actuators & Their Use in Advanced Motion Control Systems; Motion; Jul./Aug. 1995; pp. 25-27.
Park et al., "Design and Analysis of a VCA for Fuel Pump in Automobile," World of Academy of Science, Engineering and Technology; 80 2011; pp. 573-576.
U.S. Appl. No. 14/259,026, filed Apr. 22, 2014, Hartwell.
U.S. Appl. No. 14/276,983, filed May 13, 2014, Hartwell.
U.S. Appl. No. 14/232,607, filed May 21, 2014, Mumby et al.
Fleischmann et al., Vacuum Sealing: Indication, Technique, and Results, Eur J Orthop Surg Traumatol, (1995) 5:37-40.
Greer, et al., Techniques for Applying Subatmospheric Pressure Dressing to Wounds in Difficult Regions of Anatomy, JWOCN, vol. 26, No. 5, 1999 pp. 250-253.
K.F. Jeter, T.E. Tintle, and M. Chariker "Managing Draining Wounds and Fistulae: New and Established Methods" (1990) 240-246.
Kendall ULTEC Hydrocolloid Dressing (4"x4"), product ordering page, web page downloaded Jul. 13, 2014.
Protz Kerstin: "Modern Wundauflagen unterstutzen Heilungsprozess", Wundversorgung: Indikation und Anwendung, Geriatrie Journal Apr. 2005, pp. 3333-3339.
US 7,186,244, 03/2007, Hunt et al. (withdrawn)

\* cited by examiner

US 9,227,000 B2

PORTABLE WOUND THERAPY SYSTEM

CROSS-REFERENCE TO RELATED APPLICATIONS

This application is a continuation application of U.S. application Ser. No. 11/904,411, filed on Sep. 27, 2007 entitled "PORTABLE WOUND THERAPY SYSTEM", which claims the benefit of priority under 35 U.S.C §119(e) of U.S. Provisional Application No. 60/847,886, filed on Sep. 28, 2006 and entitled "PORTABLE WOUND THERAPY SYSTEM" all of which are hereby incorporated herein by reference in their entirety and are to be considered a part of this specification.

BACKGROUND

1. Technical Field

The present disclosure relates to treating an open wound, and, more specifically, relates to a portable wound therapy system including a wound dressing in conjunction with subatmospheric pressure to promote healing of the open wound.

2. Description of Related Art

Wound closure involves the migration of epithelial and subcutaneous tissue adjacent the wound towards the center and away from the base of the wound until the wound closes. Unfortunately, closure is difficult with large wounds, chronic wounds or wounds that have become infected. In such wounds, a zone of stasis (i.e. an area in which localized swelling of tissue restricts the flow of blood to the tissues) forms near the surface of the wound. Without sufficient blood flow, the epithelial and subcutaneous tissues surrounding the wound not only receive diminished oxygen and nutrients, but, are also less able to successfully fight microbial infection and, thus, are less able to close the wound naturally. Such wounds have presented difficulties to medical personnel for many years.

Negative pressure therapy also known as suction or vacuum therapy has been used for many years in treating and healing wounds. A variety of negative pressure devices have been developed to drain excess wound fluids, i.e., exudates, from the wound to protect the wound and, consequently, improve healing. Various wound dressings have been employed with the negative pressure devices to isolate the wound and maintain the subatmospheric environment.

SUMMARY

Accordingly, a portable system for subatmospheric pressure therapy in connection with healing a surgical or chronic wound, includes a wound dressing dimensioned for positioning relative to a wound bed of a subject, a portable subatmospheric pressure mechanism dimensioned to be carried or worn by the subject and a container for collecting exudates from the wound bed removed under the subatmospheric pressure supplied by the subatmospheric pressure mechanism. The portable subatmospheric pressure mechanism includes a housing, a subatmospheric pressure source disposed within the housing and in fluid communication with the wound dressing to supply subatmospheric pressure to the wound dressing and a power source mounted to or within the housing for supplying power to actuate the subatmospheric pressure source. The subatmospheric pressure source includes a pump member. The pump member is selected from the group consisting of a diaphragm pump, a double diaphragm pump, a bellows pump and a peristaltic pump.

An actuator for activating the pump member may also be provided. The actuator may be mounted to the housing. The actuator may be selected from the group consisting of AC motors, DC motors, voice coil actuators and solenoids. The power source may include disposable batteries or rechargeable batteries and may be releasably mounted to the housing. The power source may be reused with new components of the subatmospheric pressure mechanism.

The container may be mounted to or within the housing. The container may be relatively flexible. Alternatively, the flexible container may be remote from the housing and worn by the patient. The flexible container includes at least one collection path or a plurality of collection paths defined therewithin for containing the exudates. The plurality of collection paths may define a serpentine or parallel fluid path arrangement.

The subatmospheric pressure mechanism may be discarded after a single period of use. Alternatively, some of the components of the subatmospheric pressure mechanism may be reused.

The wound dressing may include a wound contact member for positioning against the wound bed, a wound packing member and a wound covering to encompass a perimeter of the wound bed. The wound contact member may include a porous section to permit passage of exudates. The wound contact member may be substantially non-adherent to the wound bed. The wound packing member may include a plurality of fibers or filaments in a tow arrangement. The wound covering may be adapted to permit passage of moisture.

BRIEF DESCRIPTION OF THE DRAWINGS

Various embodiments of the wound dressing system of the present disclosure are described herein with reference to the drawings wherein.

DESCRIPTION OF THE PREFERRED EMBODIMENTS

The wound therapy system of the present disclosure promotes healing of a wound via the use of a wound dressing and a portable subatmospheric pressure mechanism. The wound therapy system is entirely portable, i.e., it may be worn or carried by the subject such that the subject may be completely ambulatory during the therapy period. The wound therapy system including the subatmospheric pressure mechanism and components thereof may be entirely disposable after a predetermined period of use or may be individually disposable whereby some of the components are reused for a subsequent therapy application. Generally, the portable subatmospheric pressure mechanism applies subatmospheric pressure to the wound to effectively remove wound fluids or exudates captured by the composite wound dressing, and, to increase blood flow to the wound bed and enhance cellular stimulation of epithelial and subcutaneous tissue.

The wound therapy system of the present disclosure promotes healing of a wound in conjunction with subatmospheric negative pressure therapy. The system may incorporate a variety of wound dressings and subatmospheric pressure sources and pumps.

Figure 1:
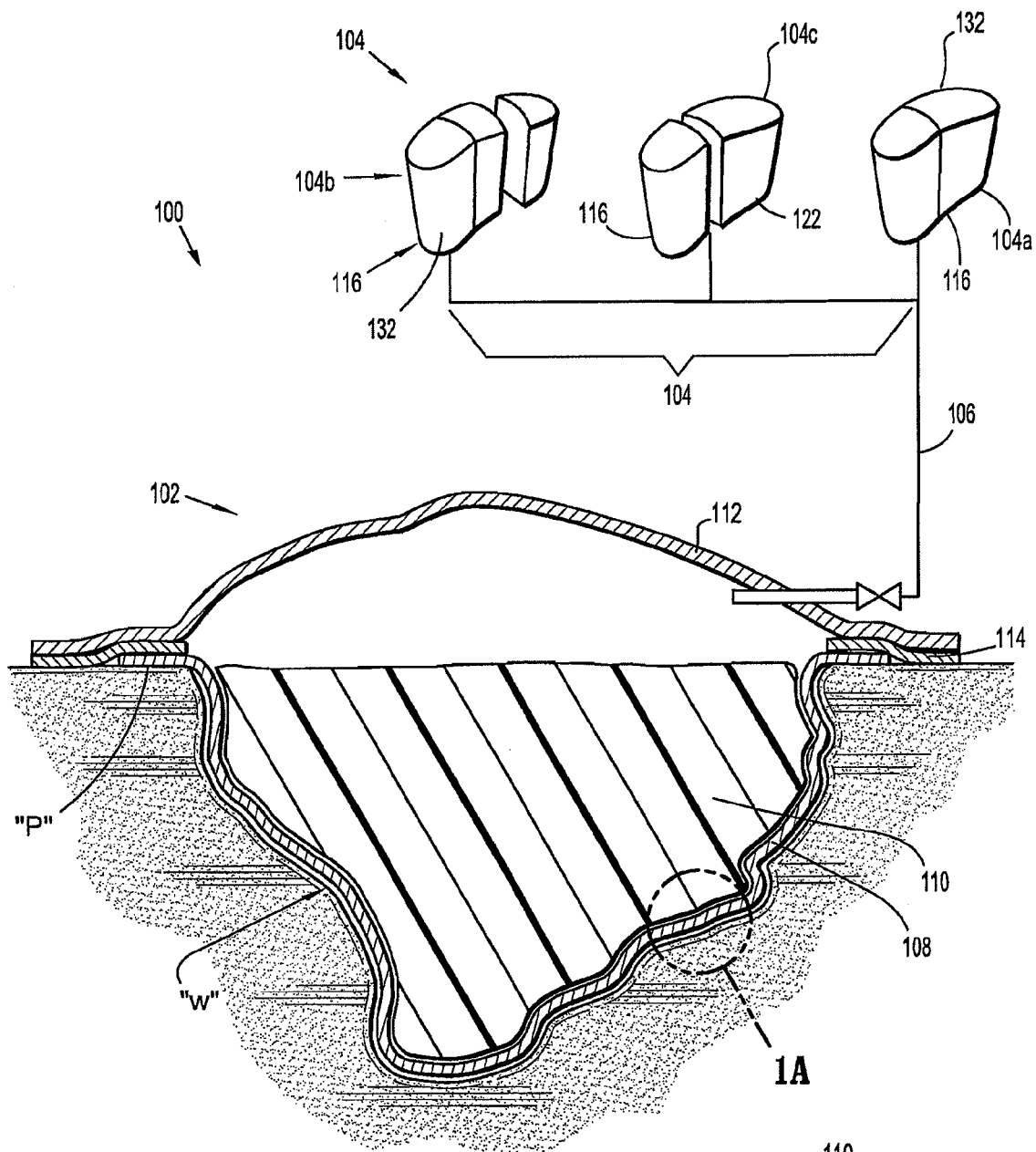
FIG. 1 is a side view in partial cross-section of the portable wound therapy mechanism of the present disclosure illustrating the wound dressing and the subatmospheric pressure mechanism.

Referring now to FIG. 1, several embodiments of the wound therapy system 100 of the present disclosure are illustrated. Wound therapy system 100 includes composite wound dressing 102 and subatmospheric pressure mechanism 104 in fluid communication with the wound dressing 102 through conduit, identified schematically as reference numeral 106. In FIG. 1, three alternate subatmospheric pressure mechanisms 104a, 104b, 104c are shown. Subatmospheric pressure mechanisms 104a, 104b, 104c share similar components as will be appreciated. Any of the subatmospheric pressure mechanisms 104a, 104b, 104c are contemplated for use with wound dressing 102.

Figure 1A:
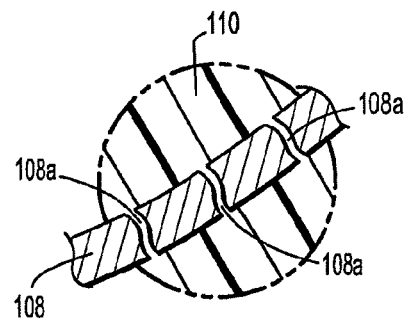
FIG. 1A is an enlarged view of the area of detail identified in FIG. 1.

Wound dressing 102 may includes several components, namely, wound contact layer or member 108, a wound packing member or filler 110 supported by the contact member 108 and outer layer or cover member 112. Wound contact member 108 is adapted to substantially conform to the topography of a wound bed "w". Wound contact member 108 is substantially porous to permit exudates to pass from the wound bed "w" through the wound contact member 108. The porosity of contact member 108 may be adjusted by varying the size of the apertures or perforations both in diameter or size and in distribution about the contact member 108. Thus, fluid flow from the wound may be optimized and adherence of the contact member 108 to the wound bed may be minimized. Wound contact member 108 may also be non-adherent. This configuration allows fluid and exudates to flow uninhibited through wound contact member 108 with minimal "sticking" of wound contact member 108 to the wound bed "w" while maintaining proper wound moisture balance. FIG. 1A illustrates contact member 108 with pores 108a. The pore 108a may be equal in size or diameter or have varying or random sizes and dimensions.

The passage of wound exudates through the wound contact member 108 is preferably unidirectional such that wound exudates do not flow back to the wound bed "w". This unidirectional flow feature could be in the form of directional apertures imparted into the material layer, a lamination of materials of different fluid transfer or wicking capability or a specific material selection that encourages directional exudates flow. However, a bidirectional layer for the purposes of supplying medicine or anti-infectives to the wound bed "w" is also envisioned and will be described hereinafter.

In addition, agents such as hydrogels and medicaments could be bonded or coated to the contact member 108 to reduce bioburden in the wound, promote healing, increase blood flow to the wound bed and reduce pain associated with dressing changes or removal. Medicaments include, for example, antimicrobial agents, growth factors, antibiotics, analgesics, nitric oxide debridement agents, oxygen enrichment and the like. Furthermore, when an analgesic is used, the analgesic could include a mechanism that would allow the release of that agent prior to dressing removal or change.

Contact member 108 may be constructed from a variety of different materials. These may include but are not limited to synthetic non absorbable polymer fibers such as carbonized polymers, polyethylene (PE), polypropylene (PP), polytetrafluoroethylene (PTFE), Nylon, arimids, Kevlar, polyethylene terephthalate (PET) or natural fibers such as cellulose. It is envisioned that contact member 108 may be transparent to allow improved visual capacity and a better view of wound bed "w". Moreover, contact member 108 may be constructed of a fabric which could be woven, nonwoven (including meltblown), knitted or composite structures such as spun bonded fabrics. Exemplary materials used as contact member 108 are sold under the trademark EXCILON™ or XEROFLOW™ both by Kendall Corp, a division of TycoHealthcare.

Wound packing member 110 of wound dressing 102 is intended to absorb and transfer wound fluid and exudates. Exemplary absorbent materials include foams, nonwoven composite fabrics, hydrogels, cellulosic fabrics, super absorbent polymers, and combinations thereof. Typically, wound packing member 110 can contain or absorb up to about 100 cubic centimeters (cc) or more of wound fluid. Preferably, the absorbent material includes the antimicrobial dressing sold under the trademark KERLIX® AMD by Kendall Corp., a division of TycoHealthcare. In one preferred embodiment, packing member 110 could be preformed or shaped to conform to varying shapes of the wound bed. Those skilled in the art will recognize that packing member 110 can be formed in any suitable shape. Packing member 110 may include multiple layers. In another performed embodiment, the packing member 110 may be constructed in layers of varying absorbent materials to assist in directional flow or exudates away from the wound.

Figure 1B:
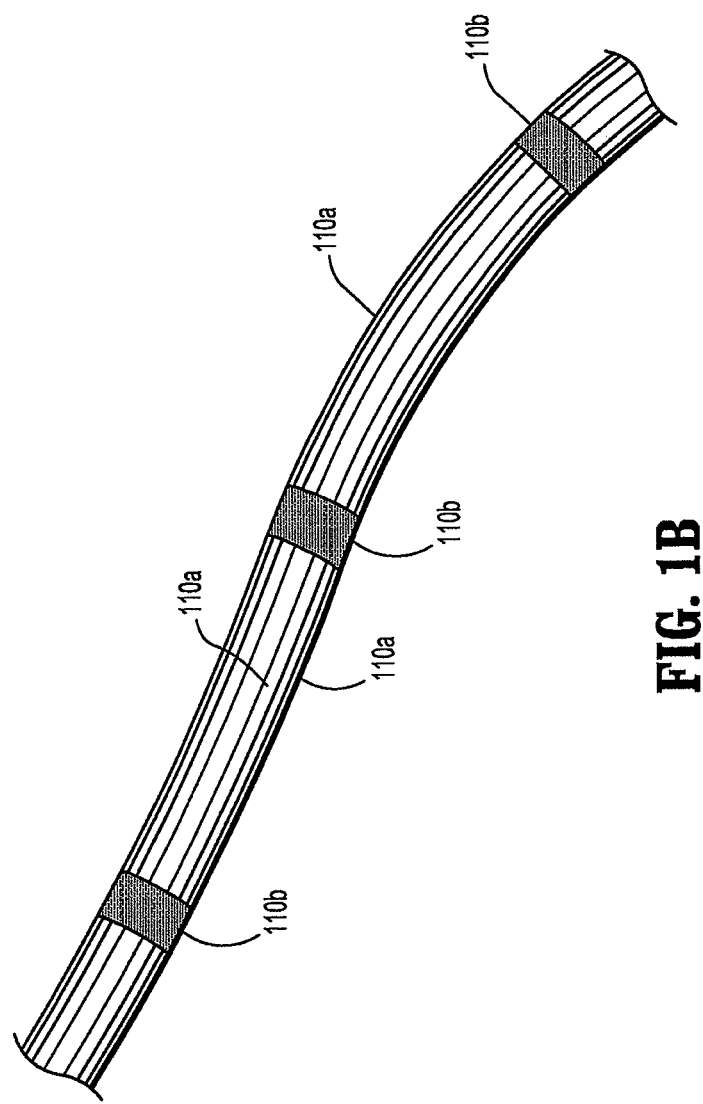
FIG. 1B is a view of an embodiment of a packing member of the wound dressing of FIG. 1.

Additionally, with reference to FIG. 1B, the packing member 110 may include hydrophobic materials such as continuous synthetic fibers intended to transfer wound fluids under negative pressure. The synthetic fibers may be constructed from polymeric materials such as polypropylene, polyethylene, polyester and other like polymers. The continuous fibers may be arranged in bundles or multiple fibers to help facilitate loft or form to the wound packing member 110, e.g., in a tow arrangement depicted in FIG. 1B. Further, the fiber bundles may be bonded at given lengths using straps or some form of adhesive, into a fused zone 110b. The fused zone 110b may be an area to cut the fiber bundle to a selected length to adapt the wound packing member 110 optimally to various wound sizes.

Alternatively, wound packing member 110 could be hydrophobic/non-absorbent materials to minimize wound fluids near the wound. Examples of such materials may be fibers in a tow arrangement, felts or foam composed of PTFE, PE, PET or hydrophilic materials treated with silicon or PTFE solution.

Additionally, absorbent or non-absorbent packing member 110 could be treated with medicaments. Medicaments include, for example, an anti-infective agent such as an antiseptic or other suitable antimicrobial or combination of antimicrobials, polyhexamethylene biguanide (hereinafter, "PHMB"), antibiotics, analgesics, healing factors such as vitamins, growth factors, nutrients and the like, as well as a flushing agent such as isotonic saline solution.

In the alternative, absorbent or non-absorbent packing member 110 may include a bead arrangement as disclosed in commonly assigned U.S. Patent Publication No. 2007/0185463, the entire contents of which is incorporated herein by reference. The beads disclosed in the '463 publication are preferably substantially rigid so as to maintain their shapes for at least a predetermined period of time during healing. The beads when arranged within the wound bed "w" define spaces or passages therebetween to permit wound exudates to pass through the passages. The sizes of the beads may vary, but they should be sized to achieve the proper pore size through the bead arrangement to facilitate cell proliferation and allow fluid and air to be evacuated from the wound. A porosity in the range of 10-1000 μm has been found beneficial in stimulating cell proliferation and in allowing fluid and air to be evacuated from the wound. The beads may work in conjunction with contact member 108 to conform to the wound bed "w" while allowing drainage of wound exudates and release of air from the wound bed "w" without clogging. As the negative pressure is applied, the beads will move and readjust their respective positions to prevent painful ingrowth that can occur with current foam dressing designs.

Referring again to FIG. 1, outer member or wound covering 112 encompasses the perimeter of the wound dressing 100 to surround wound bed "w" and to provide a liquid-tight seal around the perimeter "p" of the wound bed "w". For instance, the sealing mechanism may be any adhesive bonded to a layer that surrounds the wound bed "w". The adhesive must provide acceptable adhesion to the tissue surrounding the wound bed "w", e.g., the periwound area, and be acceptable for use on the skin without contact deteriorization (e.g., the adhesive should preferably be non-irritating and non-sensitizing). The adhesive may be permeable or semi permeable to permit the contacted skin to breathe and transmit moisture. Additionally, the adhesive could be activated or de-activated by an external stimulus such as heat or a given fluid solution or chemical reaction. Adhesives include, for example, medical grade acrylics like the adhesive used with CURAFOAM ISLAND™ dressing of TycoHealthcare Group, LP or any silicone or rubber based medical adhesives that are skin friendly and non irritating. Wound covering member 112 may be provided with an adhesive backing and/or alternatively, an adhesive may be applied to the wound covering 112 and/or skin during the procedure. As a further alternative, an annular shape adhesive member 114 may be interposed between the periphery of wound covering 112 and overlapping the periphery of contact member 108 to secure the wound covering 112 about the wound "w".

Wound covering 112 is typically a flexible material, e.g., resilient or elastomeric, that seals the top of wound dressing 102 to prevent passage of liquids or contamination to and from the wound dressing 102. Exemplary flexible materials include the semipermeable transparent dressing manufactured under the trademark Polyskin II® by Kendall Corp, a division of Tyco Healthcare Group LP. Polyskin II® is a transparent semi permeable material which permits passage of moisture or water vapors from the wound site through the dressing 102, while providing a barrier to microbes and fluid containment. Alternative films could be manufactured from polyurethanes, breathable polyolefins, copolyesters, or laminates of these materials. The transparency of wound covering 112 permits a visual review of the status of the wound dressing 102 and the saturation level of the packing member 110. As an alternative, outer covering member 112 may be impermeable to moisture vapors.

Outer suitable wound dressing are disclosed in commonly assigned U.S. Patent Publication Nos. 2007/0078366, 2007/0066946 and 2007/0055209, the entire contents of each disclosure being incorporated herein by reference.

Figure 2:
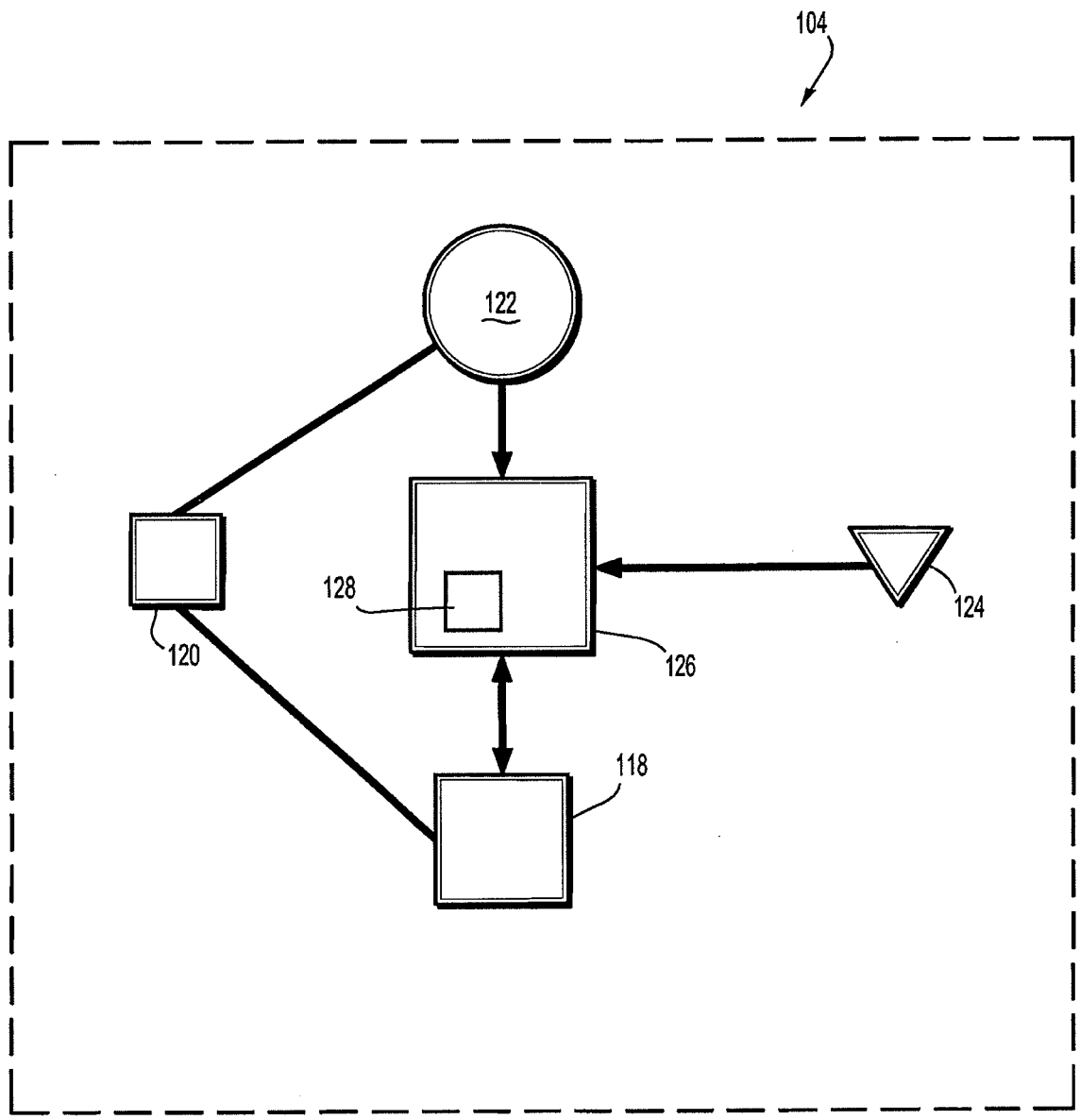
FIG. 2 is a schematic view illustrating the components of the subatmospheric pressure mechanism.

Referring now to the schematic diagram of FIG. 2, in conjunction with FIG. 1, subatmospheric pressure mechanism 104 will be discussed. Subatmospheric pressure mechanism 104 includes housing 116, vacuum source or pump 118 disposed within the housing 116, actuator or motor 120 disposed with the housing 116a for activating the vacuum source 118 and power source 122 mounted relative to the housing 114. Vacuum source or pump 118 may be any miniature pump or micropump that is biocompatible and adapted to maintain or draw adequate and therapeutic vacuum levels. Preferably, the vacuum level to be achieved is in a range between about 75 mmHg and about 125 mmHg. Vacuum source or pump 118 may be a pump of the diaphragmatic, peristaltic or bellows type or the like, in which the moving part(s) draw exudates out of the wound bed "w" into the wound dressing 102 by creating areas or zones of decreased pressure e.g., vacuum zones with the wound dressing 100. This area of decreased pressure preferably communicates with the wound bed "w" to facilitate removal of the fluids therefrom and into the absorbent or non-absorbent packing member 110. Vacuum source or pump 118 is actuated by actuator 120 which may be any means known by those skilled in the art, including, for example, AC motors, DC motors, voice coil actuators, solenoids, etc. Actuator 120 may be incorporated within pump 118.

Power source 122 may be disposed within housing 116 or separately mountable to the housing 116. A suitable power source 122 includes alkaline batteries, wet cell batteries, dry cell batteries, nickel cadmium batteries, solar generated means, lithium batteries, NiMH batteries (nickel metal hydride) each of which may be of the disposable or rechargeable variety.

Additional components of subatmospheric pressure mechanism may include pressure sensor 124 to monitor pressure adjacent the vacuum source or pump 118 or selected locations displaced from the pump 118, and regulation or control means 126. The control means 126 may incorporate a motor controller/driver 128 including processing and drive circuitry to control or vary the drive voltage to the motor of the vacuum source or pump 118 responsive to the pressure sensed by the pressure sensor 124. The output of the motor of the vacuum source 118 may be increased or decreased, or initiated or discontinued, as controlled by control means 126. Pressure sensor 124 would also provide information to assist in detecting a leak in the wound therapy system 100 if the optimal subatmospheric pressure is not achieved. Regulation or control means 126 may also have an alarm such as a visual, audio or tactile sensory alarm (e.g., vibratory etc.) to indicate to the user when specific conditions have been met (e.g., the desired vacuum level or loss of vacuum). Pressure sensor 124 may be replaced or supplemented with any other type of sensor or detector for measuring or detecting a characteristic or condition of the wound bed "w". Additional sensors contemplated include thermal sensors, bacterial sensors, oxygen sensors, moisture sensors, etc. which will provide the clinician with additional diagnostic information.

Referring again to FIG. 1, wound therapy system 100 further includes collection canister 132 which collects the exudates removed from the wound "w" during therapy through tubing 106. Collection canister 132 is preferably associated with housing 116 and may be incorporated within the housing 116 or releasably connected to the housing 116 by conventional means. Collection canister 132 is substantially rigid and defines an internal chamber in fluid communication with tubing 106. As an alternative, the collection canister 132 may include a flexible unit contained within housing 116 and removable to facilitate disposal of would fluids.

In the subatmospheric pressure mechanism 104 of FIG. 1, vacuum source or pump 118, motor 120, pressure sensor 124 and control means 126 are incorporated into housing 116. Pressure sensor 124 may also be displaced from the housing of the micropump 118, e.g., adjacent packing member 110 at a location displaced from housing 120, and connected to the control means 126 through an electrical connection. Power source 122 may be incorporated within housing 116 or may be releasably connected to the housing 116 through conventional means.

In the embodiment of subatmospheric pressure mechanism 104a, the subatmospheric mechanism 104a is intended for a single use application, i.e., the subatmospheric mechanism 104a is disposed after a predetermined period of time. Such period of time may vary from about one day to about seven days or more. One application contemplated is a three-day time period. Thus, after three days of therapy, the entire subatmospheric mechanism 104a including the components (vacuum source or pump 118, actuator or motor 120, power source 122, pressure sensor 124 and control means 126) as well as wound dressing 102, collection canister 132 and tubing 106 are disposed. In the embodiment of subatmospheric mechanism 104b, all of the components (vacuum source or pump 118, actuator or motor 120, pressure sensor 124, control means 126 and collection canister 132) are disposed after the predetermined period of time, e.g., from about one day to about seven days, with the exception of power source 122. In this regard, power source 122 has a greater life capacity, e.g., a duration of about twenty to about forty days, or more about 30 days. Thus, power source 122 may be releasably mounted to housing as shown in FIG. 1, and reconnected to the housing 116 for a subsequent application with the new components. Any means for releasably mounting power source 122 to housing may be appreciated by one skilled in the art. Power source 122 may be rechargeable.

In the embodiment of subatmospheric pressure mechanism 104c, the electrical components will have a greater life expectancy, e.g., between about twenty to about forty day, more about thirty days. Thus, these components may be reused for a subsequent application after collection canister 132, wound dressing 102 and tubing 106 are discarded.

Figure 3A:
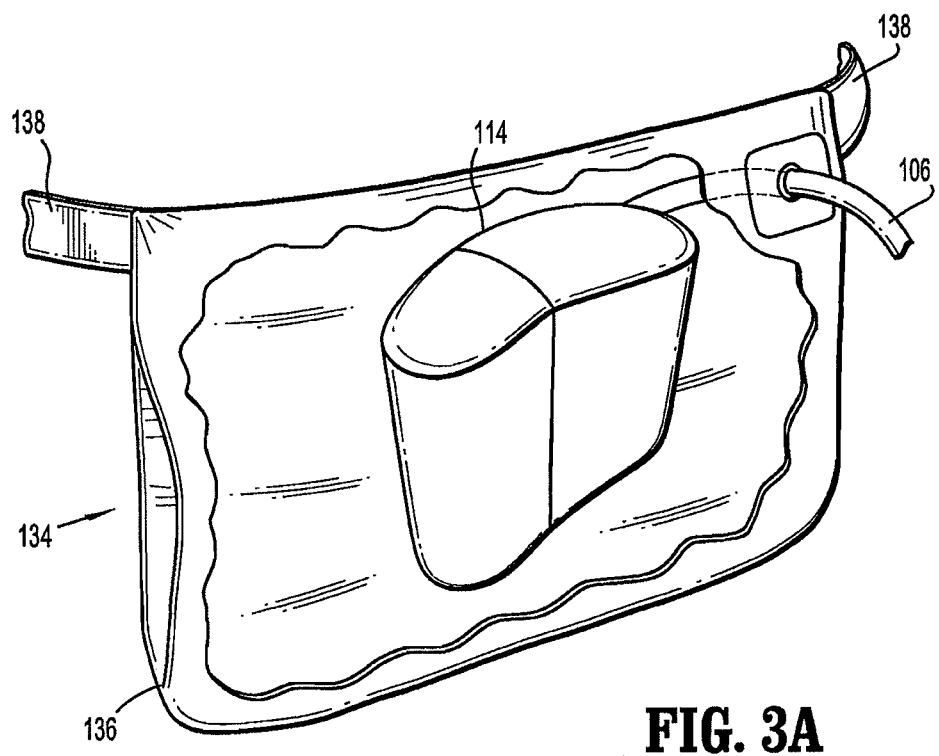
FIG. 3A is a view of a carrier support apparatus for supporting components of the subatmospheric pressure mechanism.

With reference now to FIG. 3A, there is illustrated a body support bag 134 for supporting at least the subatmospheric pressure mechanism 104 and at least canister 132. As discussed, the wound therapy system 100 of the present disclosure is adapted for mounting to the body of the patient to be a self contained portal unit. In this regard, the subatmospheric pump mechanism and canister may be at least partially carried or supported by the body support bag 134. The body support bag 134 generally includes a pouch 136 and at least one strap 138, preferably two straps, for securing the pouch 136 to the body of the patient. The body support bag 134 is intended to receive and store at least subatmospheric pump mechanism 104 and collection canister 132. The body support bag 134 may be worn about the waist of the patient such as with a belt loop. This is desirable in that it may reduce the length of tubing needed depending on the location of the wound. In addition, the pouch 136 may be located adjacent the abdomen of the patient which may present a significantly enhanced ability to conceal the system. Tubing 106 may be secured to the body with tape, straps, or the like, or, optionally, may be unsecured and disposed beneath the patient's clothing. Thus, the body support bag 134 permits the patient to move without restrictions or limitations, and provides an entirely portable capability to the patient during wound drainage and healing.

Figure 3B:
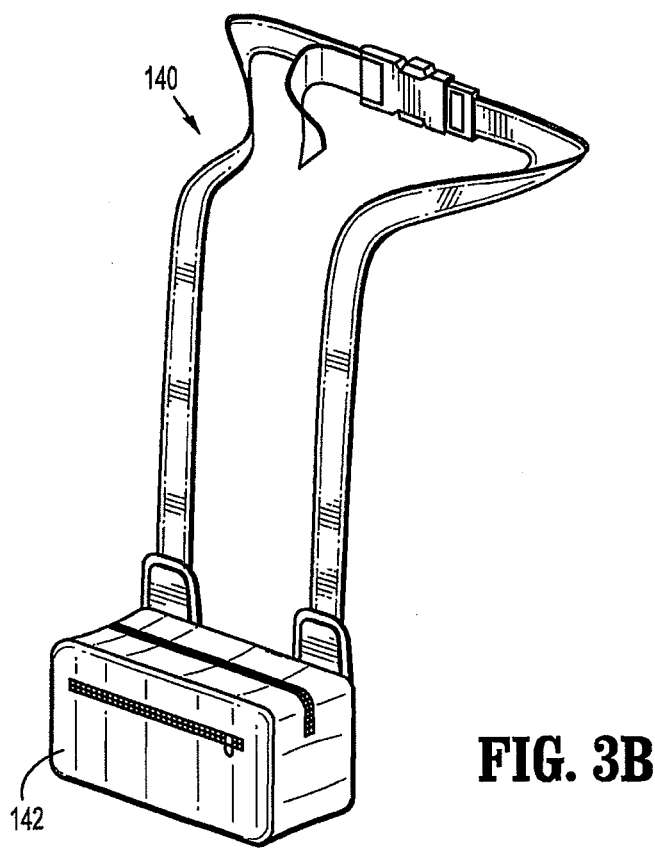
FIG. 3B is a view of an alternate carrier support apparatus.

FIG. 3B illustrates an alternate embodiment of the body support bag. In accordance with this embodiment, the body support bag 140 is adapted for mounting to the shoulder of the patient and has a pouch 142. In other respects, the body support bag 140 functions in a similar manner to the body support bag of FIG. 3.

Figure 4:
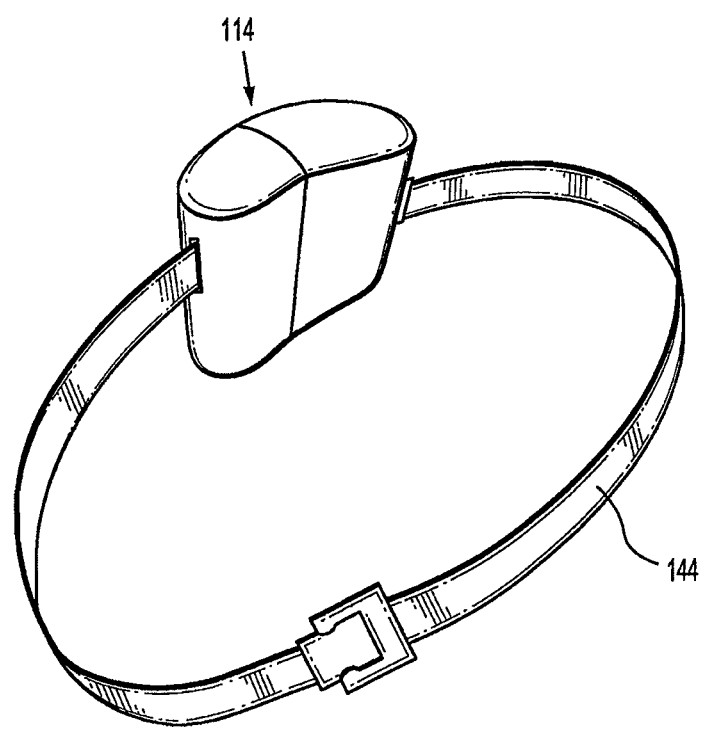
FIG. 4 is a view of another alternate carrier support apparatus.

FIG. 4 illustrates an arrangement where the body support bags 134, 140 are eliminated. In this arrangement, a belt 144 is connected to housing 114 through conventional means such as, e.g., a slide clasp, to permit the housing 114 to slide relative to the belt 144, or, alternatively, the belt 144 may be directly fixed to the housing 114. Multiple belt arrangements are also envisioned.

In use, wound dressing is placed adjacent the wound bed "w" as shown in FIG. 1. Subatmospheric pressure mechanism 104 is then activated creating a reduced pressure state within wound dressing 102. As the pumping progresses, exudates are collected and directed to collection canister 132. When vacuum source or pump 118 is activated and set at a specific set point, the pump 118 will begin to draw pressure until it achieves the set point. The vacuum reading at the pump will stay at this level until the set point is changed, the pump is turned off, or there is a major leak in the system that overcomes the pumps ability to continue to achieve this level. Subatmospheric pressure therapy may be continuous or intermittent.

Figure 5C:
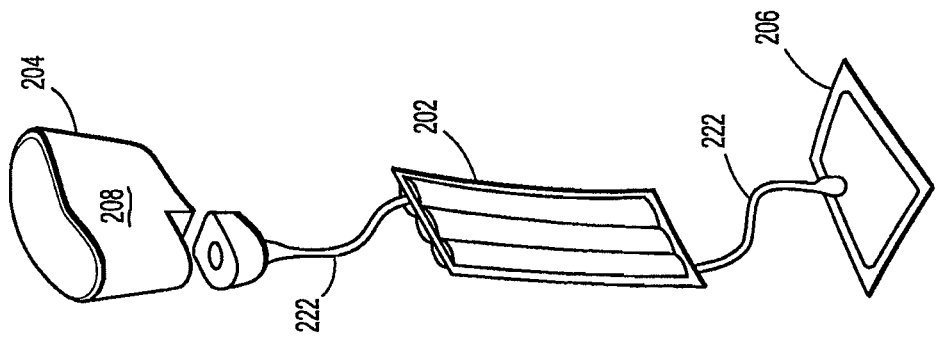
FIGS. 5A-5C are views of alternate embodiments of the portable wound therapy system illustrating the wound dressing and a flexible exudates container for collecting exudates.
Figure 5B:
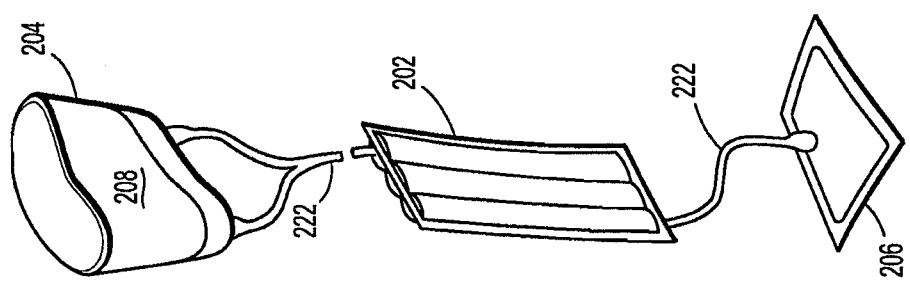
Figure 5A:
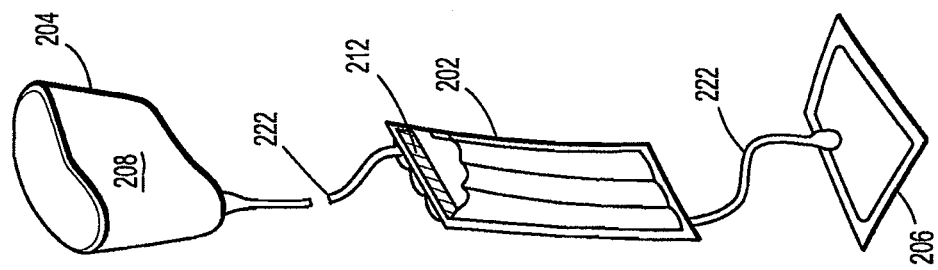
Figure 6:
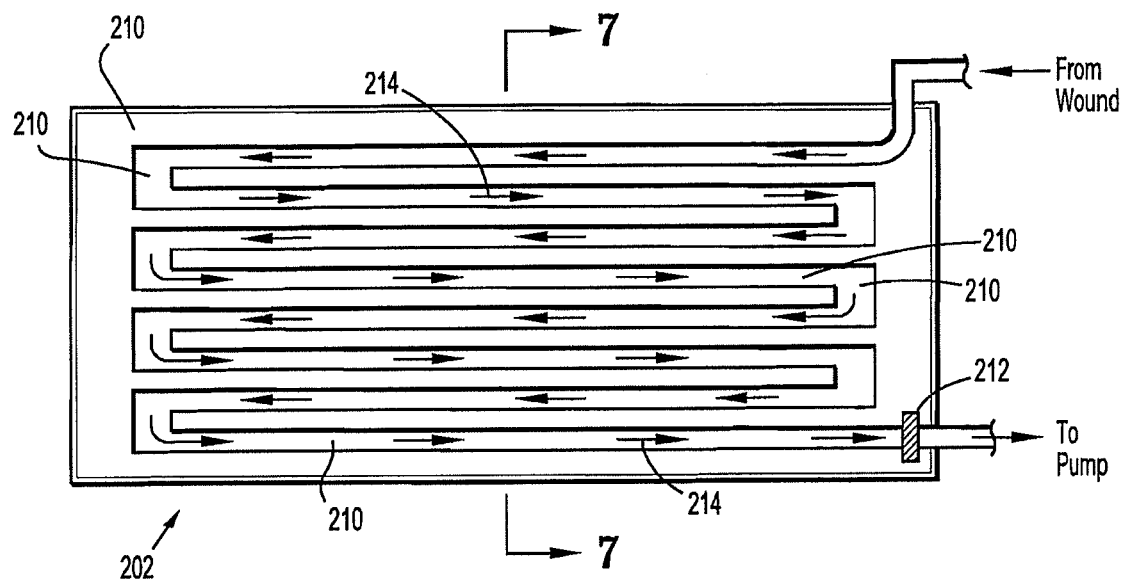
FIG. 6 is a top plan view of the flexible exudates container of the embodiments of FIGS. 5A-5C.
Figure 7:
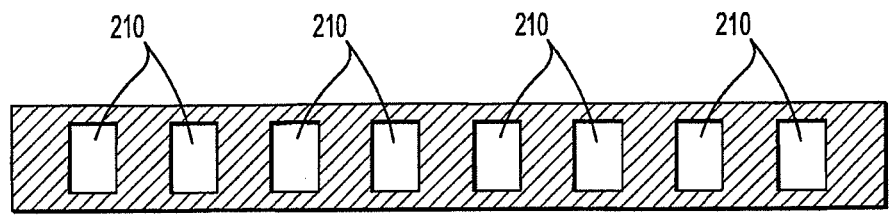
FIG. 7 is a cross-sectional view of the flexible exudates container taken along the lines 7-7 of FIG. 6.

FIGS. 5A-5C illustrates alternative embodiments of the wound therapy system 200 of the present disclosure. In accordance with these embodiments, collection container 202 is removed from housing 204 and is disposed in line between wound dressing 206 and subatmospheric pressure mechanism 208. Various containers 202 are contemplated. In one embodiment, container 202 is relatively flexible and expandable, and defines an internal chamber for collecting the exudates. Thus, as exudates are received within container 202, the container 202 expands to accommodate the volume of exudates. Container 202 may include multiple chambers. In one embodiment shown in FIGS. 5A-5C and FIGS. 6-7, container 202 includes multiple channels or collection paths 210 in fluid communication with each other. Channels 210 may be arranged in side by side relation as shown to thereby define a general sinusoidal arrangement. Container 202 may include super absorbent materials within the internal chamber or collection paths 210 such as superabsorbent polymers or gels, i.e., a polymer having the capacity to absorb liquid to an amount several times larger than its own weight. Antimicrobials to control bacteria growth may also be added to container 202. The use of such polymers will significantly enhance the absorbent capability and exudates volume contained within the container 202. Container 202 also may include a filtration membrane 212 adjacent the exit port leading to the pump or housing 204 to minimize passage of exudates to the pump. Suitable filtration membranes 212 include membrane filters incorporating polymer films with specific pore ratings. Such polymer films may include nitrocellulose, cellulose acetate, hydrophilic PTFE, hydrophobic PTFE, nylon, polycarbonate. FIG. 5A illustrates a portion of container 202 removed to depict the location of filtration membrane 212. The fluid flow of exudates is indicated by directional arrows 214.

Figure 8:
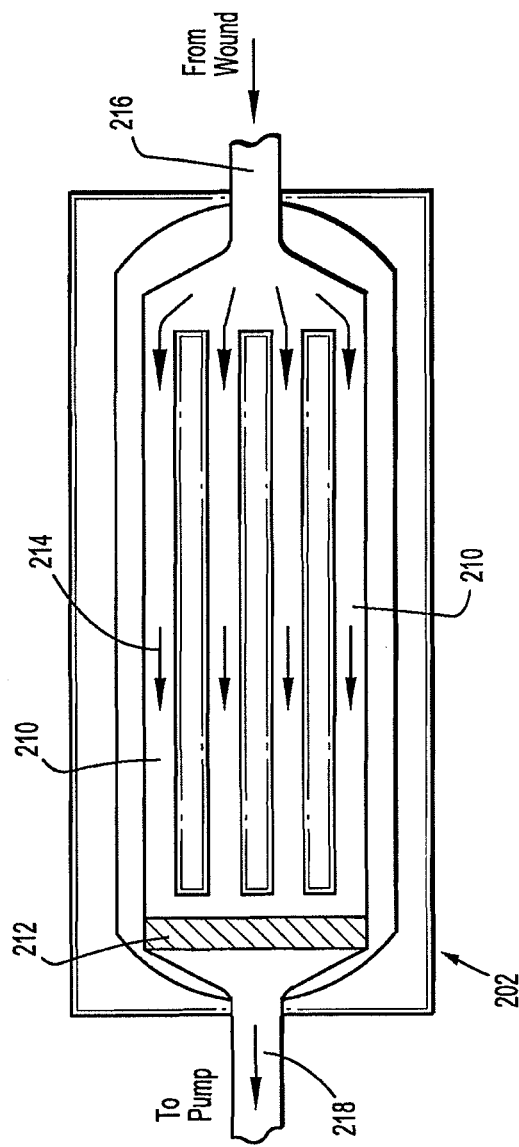
FIG. 8 is a top plan view of an alternate arrangement of the flexible exudates container incorporating a substantially parallel fluid path.

FIG. 8 illustrates an alternate arrangement where channels 210 extend in general parallel arrangement within the container 202 along a major portion of the channels 210. The channels 210 are in communication with inlet and outlet vacuum conduits 216, 218 which are in communication with the respective wound dressing 102 and the pump 118. Non-absorbent materials may also be added. Such materials may include TOW, felt or foam.

Figure 9:
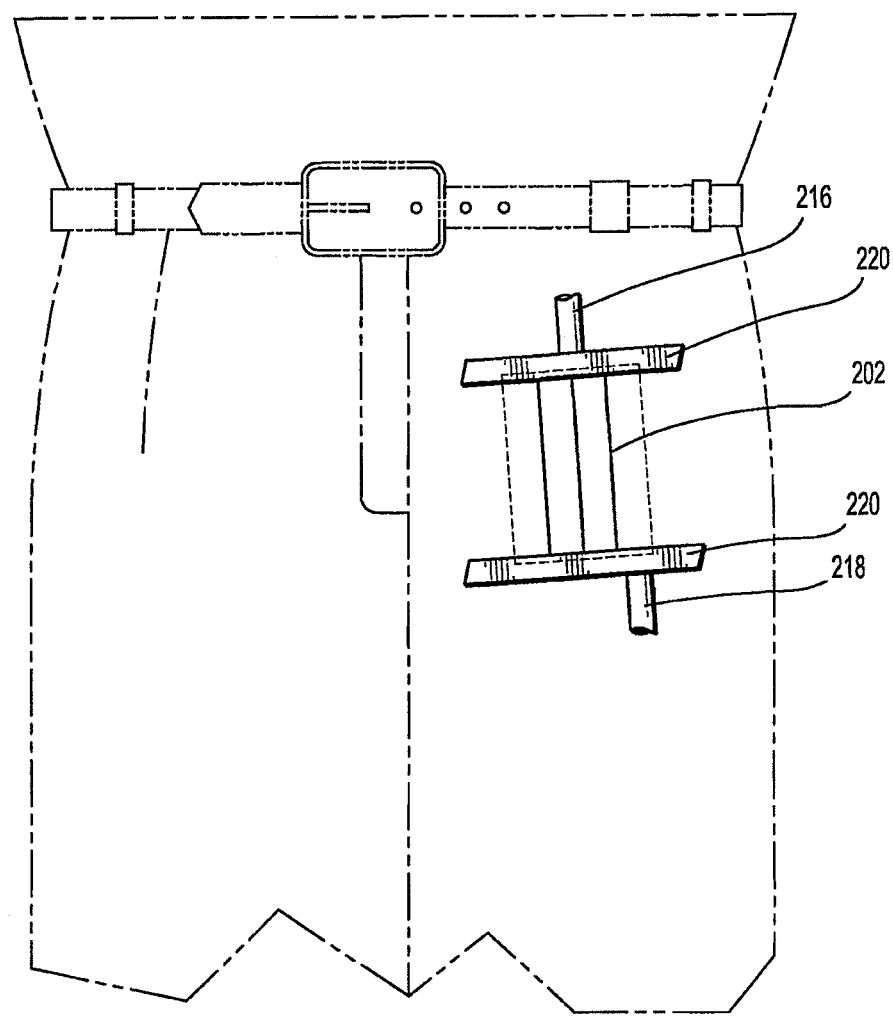
FIG. 9 is a view illustrating one methodology for mounting the flexible exudates container to the subject.

Container 202 may be supported via either of the body support bags illustrated in FIGS. 3-4. Alternatively, as shown in FIG. 9, container 202 may be directly affixed to the subject by conventional means including via surgical tape 220 or leg straps (elastic straps). Container 202 may be affixed to the leg area, abdominal area, back area or any inconspicuous location on the body or on or near the wound dressing.

In the embodiment of FIG. 5A, container 202, wound dressing 206 and tubing 222 are intended to be replaced after a predetermined period of time which extends between about one to about seven days, more about three days. Subatmospheric pressure mechanism 104d including vacuum source or pump, actuator or motor, power source, pressure sensor, control means (similar to the corresponding components discussed hereinabove) are intended for an extended life, for example between about twenty to about forty days, more about thirty days. Thus after, e.g., each three day period, container 202, tubing 222 and wound dressing 202 are discarded and replaced with new components for connection to subatmospheric pressure mechanism. In the embodiment of FIG. 5B, container 202, tubing 222 and wound dressing 206 will be replaced as discussed hereinabove in connection with the embodiment of FIG. 5A. Similarly, the components of subatmospheric pressure mechanism will be replaced in a similar manner. However, subatmospheric pressure mechanism 104e is a more advanced system and may include a double diaphragm pump operated via a voice coil actuator. Passive dampening capabilities such as foam insulation to reduce the noise levels may also be incorporated into the housing. In the embodiment of FIG. 5C, container 202, tubing 222 and wound dressing 206 as well as vacuum source or pump and sensor are disposable in a shorter duration of from about one to about seven days, or about three days. The power source, actuator or motor and control means are intended for reuse with new components replacing the earlier discarded components.

While the disclosure has been illustrated and described, it is not intended to be limited to the details shown, since various modifications and substitutions can be made without departing in any way from the spirit of the present disclosure. As such, further modifications and equivalents of the invention herein disclosed can occur to persons skilled in the art using no more than routine experimentation, and all such modifications and equivalents are believed to be within the spirit and scope of the disclosure as defined by the following claims.

What is claimed is:

1. A portable system for subatmospheric pressure therapy in connection with healing a wound, which comprises:
   a wound dressing dimensioned for positioning over the wound, wherein the wound dressing comprises a filler and a wound cover configured to surround a perimeter of the wound;
   a portable subatmospheric pressure mechanism comprising:
      a housing; and
      a subatmospheric pressure source disposed within the housing and configured to be in fluid communication with the wound dressing to supply subatmospheric pressure to the wound dressing, the subatmospheric pressure source including a pump; and
   a plurality of channels configured to be disposed between the wound dressing and the subatmospheric pressure mechanism, the plurality of channels including an inlet port for receiving exudates removed from the wound and an outlet port in communication with the subatmospheric pressure source, wherein the plurality of channels are predetermined channels and are arranged in a general parallel relation along a major portion of the respective lengths of the channels, the plurality of channels in fluid communication with each other,
   wherein at least one of the plurality of channels comprises a non-absorbent material, and
   wherein the plurality of channels are made of a flexible material configured to enclose the non-absorbent material.

2. The portable system according to claim 1, further comprising a container for collecting exudates from the wound removed under the subatmospheric pressure supplied by the subatmospheric pressure source.

3. The portable system according to claim 2, wherein the container is relatively flexible.

4. The portable system according to claim 3, wherein the flexible container includes at least one collection path defined therewithin for containing the exudates.

5. The portable system according to claim 1, wherein the pump is selected from the group consisting of a diaphragm pump, a double diaphragm pump, a bellows pump, a voice coil pump, and a peristaltic pump.

6. The portable system according to claim 5, wherein the voice coil pump comprises a voice coil actuator for activating the pump and the voice coil actuator is mounted to the housing.

7. The portable system according to claim 1, wherein the plurality of channels are dimensioned to be worn by the subject.

8. The portable system according to claim 1, wherein the portable subatmospheric pressure mechanism is adapted to be discarded after a single use.

9. The portable system according to claim 1, wherein the wound dressing includes a wound contact layer configured to be positioned in contact with the wound.

10. The portable system according to claim 9, wherein the wound contact layer includes a porous section to permit passage of exudates.

11. The portable system according to claim 9, wherein the wound contact layer is substantially non-adherent to the wound.

12. The portable system according to claim 1, wherein the filler includes a plurality of fibers or filaments in a tow arrangement.

13. The portable system according to claim 1, wherein the wound cover is adapted to permit passage of moisture.

14. The portable system according to claim 1, wherein the filler comprises multiple absorbent layers of varying absorbent materials to assist in directional flow of exudates away from the wound.

15. The portable system according to claim 1, wherein the filler comprises multiple layers of absorbent and non-absorbent material.

16. The portable system according to claim 15, wherein the absorbent material comprises super absorbent polymers.

17. The portable system according to claim 1, wherein the plurality of channels comprise at least two channels.

18. The portable system according to claim 1, comprising a membrane filter adjacent the outlet port to minimize passage of the exudates toward the subatmospheric pressure source.

19. The portable system according to claim 1, wherein the non-absorbent material comprises foam.

20. The portable system according to claim 1, further comprising a power source configured to supply power to actuate the subatmospheric pressure source.

21. The portable system according to claim 20, wherein the power source is releasably mounted relative to the housing, and is intended for reuse after the subatmospheric pressure source is discarded.

\* \* \* \* \*